Figure 1:
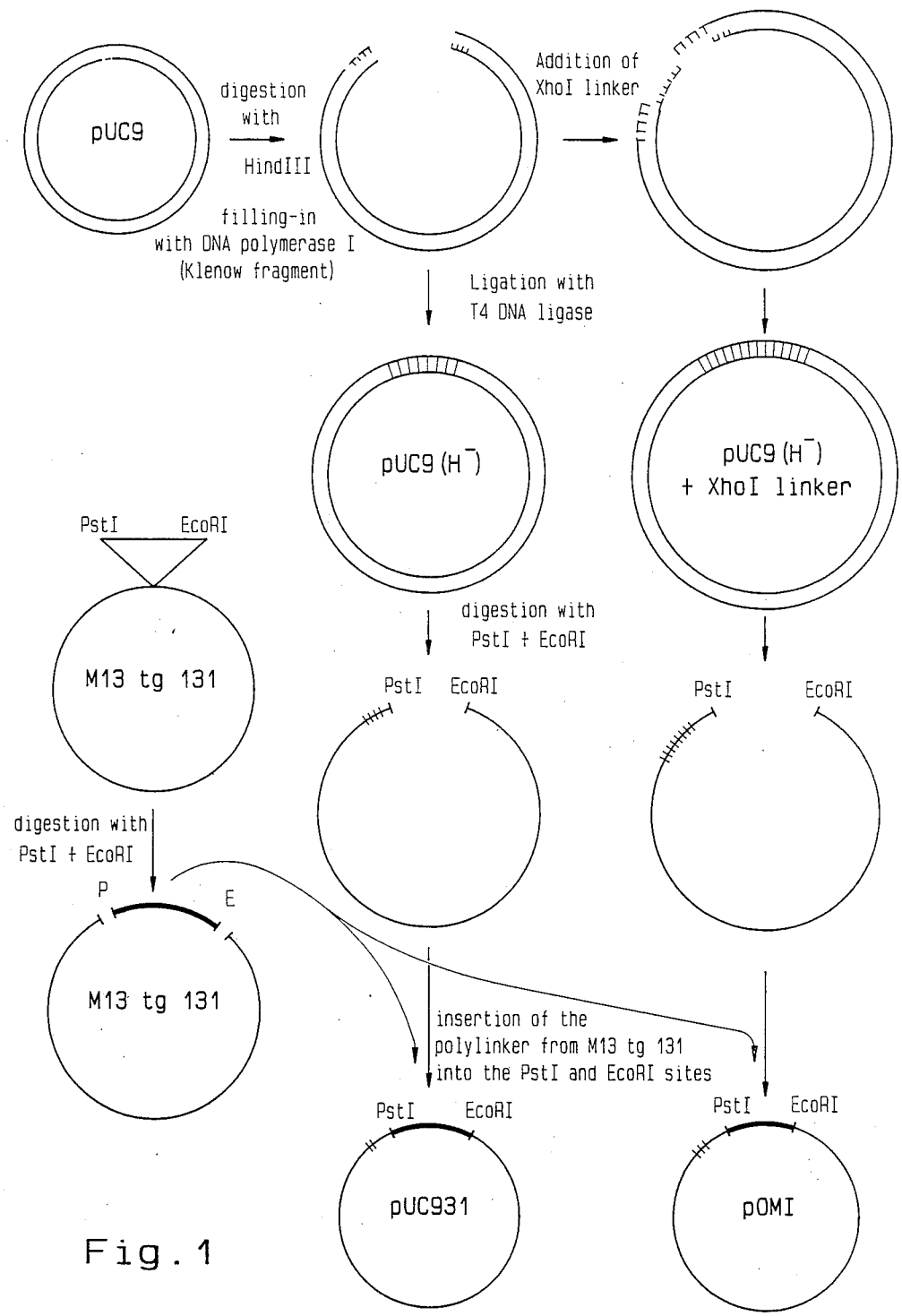

United States Patent [19]

Oberbäumer

[11] Patent Number: 4,985,359
[45] Date of Patent: Jan. 15, 1991

[54] VECTORS AND METHODS FOR THE CONSTRUCTION OF CDNA LIBRARIES

[75] Inventor: Ilse Oberbäumer, Burgfriedenstr. 8, D-8033 Krailling, Fed. Rep. of Germany

[73] Assignee: Ilse Oberbäumer, Krailling, Fed. Rep. of Germany

[21] Appl. No.: 57,520

[22] PCT Filed: Sep. 25, 1986

[86] PCT No.: PCT/EP86/00604
§ 371 Date: Jul. 23, 1987
§ 102(e) Date: Jul. 23, 1987

[87] PCT Pub. No.: WO87/02057
PCT Pub. Date: Apr. 9, 1987

[30] Foreign Application Priority Data

Sep. 26, 1985 [DE] Fed. Rep. of Germany ....... 3534359

[51] Int. Cl.$^5$ .......................... C12N 1/15; C12N 1/21; C12N 15/10; C12N 15/64
[52] U.S. Cl. .................... 435/172.3; 435/91; 435/172.1; 435/252.3; 435/254; 435/255; 435/240.2; 435/320; 536/27; 935/6; 935/22; 935/52; 935/54; 935/66; 935/76; 935/77; 935/79; 935/80
[58] Field of Search ..................... 435/91, 172.1, 172.3, 435/252.3, 254, 240.2, 320, 255; 536/27; 935/1, 6, 16, 17, 18, 22, 23, 24, 27, 28, 29, 52, 55, 66, 68, 69, 72, 73, 74, 75, 76, 79, 80

[56] References Cited

U.S. PATENT DOCUMENTS 4,394,443 7/1983 Weissman et al. ....................... 435/6

OTHER PUBLICATIONS

Maniatis et al., 1982, Molecular Cloning, Cold Spring Harbor Laboratory, pp. 148, 217–229, 239 and 241.
BRL Catalogue and Reference Guide, 1985, Bethesda Research Laboratories, p. 55.
Okayama, H. and Berg, P., *Molec. Cell. Biol.* 2:161–170 (1982).
Coleclough, C. and Erlitz, F. L., *Gene* 34: 305–314 (1985).
Heidecker, G. and Messing, J., *N. Acids Res.* 11: 4891–4906 (1983).

*Primary Examiner*—Richard A. Schwartz
*Assistant Examiner*—Richard C. Peet
*Attorney, Agent, or Firm*—Saidman, Sterne, Kessler & Goldstein

[57] ABSTRACT

Vectors useful in the construction of cDNA libraries and methods for constructing these vectors are disclosed. According to the invention, a vector includes a polylinker region which is cut to linearize the vector. Oligo(dC) tails having terminal dideoxynucleotides are added to the two 3' ends of the vector. One oligo(dC) tail is removed and replaced with oligo(dT) to which poly(A) mRNA is annealed. The first complementary DNA strand is synthesized and tailed with oligo(dG), which anneals with the remaining oligo(dC) tail, thus circularizing the vector. The mRNA is digested and the second cDNA strand synthesized. Alternatively, the second cDNA strand can be synthesized before circularizing the vector. The resulting vector is used to transform microorganisms to create a cDNA library. The cDNA can be recovered by cleaving the vector at sites within the polylinker sequence.

11 Claims, 8 Drawing Sheets pUC931
                                           PstI  SalI  BamHI  HindIII  XbaI  KpnI  SphI  EcoRV  SacI      SmaI  EcoRI
1  ATGACCATGATTACGCCAAGCTAGCTTGGCTGCAGGTCGACGGATCCCAAGCTTCTCTAGAGGTACCGCATGCGATATCGAGCTCTCCCGGGAATTCACTG  102
   T  M  I  T  P  S  *  L  G  C  R  S  T  D  P  K  L  L  L  E  V  P  H  A  I  S  S  S  P  G  N  S  L pOM9
                        PstI  SalI  BamHI  HindIII  XbaI  KpnI  SphI  EcoRV  SacI      SmaI  EcoRI
1  ATGACCATGATTACGCCAATTGGCTGCAGGTCGACGGATCCCAAGCTTCTCTAGAGGTACCGCATGCGATATCGAGCTCTCCCGGGAATTCACTG  96
   T  M  I  T  P  I  G  C  R  S  T  D  P  K  L  L  L  E  V  P  H  A  I  S  S  S  P  G  N  S  L pOM3
                     ClaI              PstI  SalI  BamHI  HindIII  XbaI  KpnI  SphI  EcoRV  SacI      SmaI  EcoRI
1  ATGACCATGATTACGCCACATCGATGGCTTGGCTGCAGGTCGACGGATCCCAAGCTTCTCTAGAGGTACCGCATGCGATATCGAGCTCTCCCGGGAATTCACTG  105
   T  M  I  T  P  H  R  W  L  G  C  R  S  T  D  P  K  L  L  L  E  V  P  H  A  I  S  S  S  P  G  N  S  L pOM1
                        XhoI              PstI  SalI  BamHI  HindIII  XbaI  KpnI  SphI  EcoRV  SacI      SmaI  EcoRI
1  ATGACCATGATTACGCCAAGCTCTCGAGAGCTTGGCTGCAGGTCGACGGATCCCAAGCTTCTCTAGAGGTACCGCATGCGATATCGAGCTCTCCCGGGAATTCACTG  108
   T  M  I  T  P  S  S  S  R  E  L  G  C  R  S  T  D  P  K  L  L  L  E  V  P  H  A  I  S  S  S  P  G  N  S  L

Fig. 2 pUCB30

1 ATGACCATGATTACGAATTCCCGGGAGAGCTCGATATCGCATGCGGTACCTCTAGAAGAAGCTTGGGATCCGTCGACCTGCAGCCAAGCTAGCTTGGCACTGGCC 105
  T  M  I  T  N  S  R  E  S  S  I  S  H  A  V  P  L  E  E  A  W  D  P  S  T  C  S  Q  A  S  L  A  L  A

EcoRI  SmaI  SacI  EcoRV  SphI  KpnI  XbaI  HindIII  BamHI  SalI  PstI pOMB

1 ATGACCATGATTACGAATTCCCGGGAGAGCTCGATATCGCATGCGGTACCTCTAGAAGAAGCTTGGGATCCGTCGACCTGCAGCCAATTGGCACTGGCC 99
  T  M  I  T  N  S  R  E  S  S  I  S  H  A  V  P  L  E  E  A  W  D  P  S  T  C  S  Q  L  A  L  A

EcoRI  SmaI  SacI  EcoRV  SphI  KpnI  XbaI  HindIII  BamHI  SalI  PstI pOM4

1 ATGACCATGATTACGAATTCCCGGGAGAGCTCGATATCGCATGCGGTACCTCTAGAAGAAGCTTGGGATCCGTACCTGCAGCCAAGCCATCGATTGGCACTGGCC 108
  T  M  I  T  N  S  R  E  S  S  I  S  H  A  V  P  L  E  E  A  W  D  P  S  T  C  S  Q  A  I  D  W  A  L  A

EcoRI  SmaI  SacI  EcoRV  SphI  KpnI  XbaI  HindIII  BamHI  SalI  PstI  ClaI pOM2

1 ATGACCATGATTACGAATTCCCGGGAGAGCTCGATATCGCATGCGGTACCTCTAGAAGAAGCTTGGGATCCGTCGACCTGCAGCCAAGCTCTCGAGAGCTTGGCACTGGCC 111
  T  M  I  T  N  S  R  E  S  S  I  S  H  A  V  P  L  E  E  A  W  D  P  S  T  C  S  Q  A  L  E  S  L  A  L  A

EcoRI  SmaI  SacI  EcoRV  SphI  KpnI  XbaI  HindIII  BamHI  SalI  PstI  XhoI

Fig. 3

VECTORS AND METHODS FOR THE CONSTRUCTION OF cDNA LIBRARIES

The invention concerns vectors for the construction of cDNA libraries and methods for constructing these vectors. In addition, the invention concerns methods for the construction of cDNA libraries with vectors according to the invention as well as the expression of genes in cDNA libraries constructed this way and microorganisms transformed with either the above mentioned vectors or with these vectors containing recombinant DNA.

In recent years, development of recombinant DNA methodology has permitted cloning and isolation as well as expression of genes which code for valuable products. If partial or complete primary sequence information of a gene product (e.g. protein) is available, synthetic oligodeoxynucleotide probes can be made which code for some of the known amino acid residues of the desired gene product. These oligonucleotide probes can then be used for screening of cDNA libraries for the gene coding for the protein. If the genetic information for the protein of interest is expressed in such libraries, antibodies against that protein can also be used for screening of the libraries.

Methods have been developed for cloning mRNA (messenger RNA) from cells which synthesize the protein of interest. As mRNA cannot be cloned directly, it has to be transcribed into the corresponding cDNA first. For this transcription an enzyme from a tumor virus is used, known as reverse transcriptase. Use of this enzyme and several additional procedures results in recombinant vector molecules which contain double-stranded cDNA derived from mRNA. The assembly of all these recombinant vectors which contain cDNA is called a cDNA library.

Figure 7:
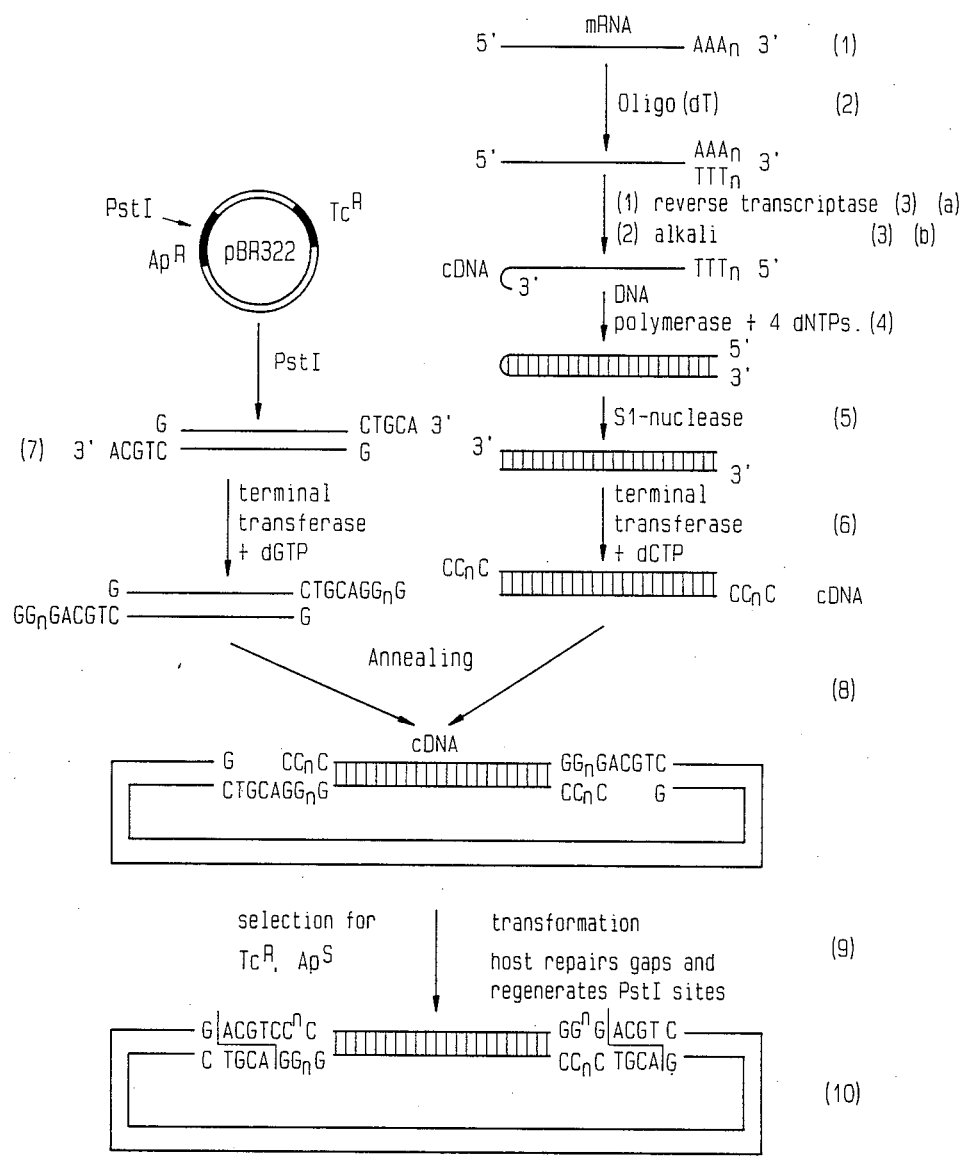

FIG. 7 illustrates the classical method for constructing cDNA libraries. In this method mRNA is first isolated from certain cells (1) and is then treated with different enzymes and alkali in successive steps of the process (steps (2) to (6)). In parallel the Yector (e.g. plasmid pBR322) is treated in such a way that insertion of the cDNA synthesized is possible. After annealing of cDNA and pretreated vector, a suitable host (e.g. strain of E. coli K12) is transformed with the vector-cDNA constructs, plated on suitable substrates and incubated. All colonies from transformed cells obtained in this way constitute a cDNA library as mentioned above.

This method for constructing cDNA libraries has the disadvantage that the mRNA isolated from the cells is subjected to several treatments (steps (1) to (6)). As an mRNA molecule is relatively labile, it is degraded to shorter pieces which lead to relatively short cDNA inserts in the order of 300 to 1000 bp (base pairs). This implies that the genetic information of proteins with more than 300 amino acids is rarely obtained completely from such libraries. Another disadvantage of the method shown in FIG. 7 results from the fact that the orientation of the cDNA in the vector cannot be directed. Therefore recombinant plasmids with cDNA in the wrong orientation cannot be detected by screening with antibodies.

The method of H. Okayama and P. Berg (Mol. Cell. Biol. 2 (1982), 161-170) allows the oriented insertion of the cDNA copies from the isolated cellular mRNA. This method is summarized in FIG. 8. This process starts with cutting the vector molecule with a restriction endonuclease and adding oligo(dT) tails to the vector with the enzyme terminal deoxynucleotidyl transferase. This results in a linearized vector molecule with oligo(dT) tails at both 3' ends. One of the (oligo)dT tails is then removed by cutting with the restriction endonuclease HpaI.

In the following step the mRNA is annealed via its poly(A) tail to the now unique oligo(dT) tail of the vector. The orientation of the annealed mRNA is predetermined as only one oligo(dT) tail is left on the manipulated vector and the mRNA contains a poly(A) tail only at its 3' end. During further steps of the procedure, the corresponding cDNA is constructed with the help of different enzymes (cf., FIG. 8), resulting finally in a circular recombinant vector molecule.

This method has the disadvantage that the addition of oligo(dC) tails (cf., FIG. 8) is impeded because the cDNA strand copied from the mRNA normally does not have full length and therefore presents a recessed 3' end.

As a consequence of this problem with adding oligo(dC) tails the yield of end products, e g. of recombinant vectors with a cDNA insert, will be low.

An additional disadvantage of this method results from the need to cut with the restriction endonuclease HindIII after first strand synthesis. During this step, also HindIII sites in the DNA/RNA hybrid will be cut, albeit with lower efficiency. If the DNA/RNA hybrid was cut, the oligo(dC) tail on the first cDNA strand is also cut off and these molecules cannot be processed any further. These digestions again lower the yield of end product.

Finally it is another disadvantage of this method that a concentration effect occurs when inserting the HindIII linker with its oligo(dG) tail. If the concentration of this linker (cf., FIG. 8) is not chosen correctly, again the yield of recombinant vectors with a cDNA insert will be low for this method.

The invention therefore aims at providing vectors and methods which allow the construction of cDNA libraries with high efficiency, containing recombinant plasmids with large cDNA inserts in a predetermined orientation.

The subject of the invention is therefore a linearized vector characterized in that it contains an oligo(dT) tail at one 3' end and an oligo(dC) or oligo(dG) tail with a terminal dideoxynucleotide residue at the other 3' end.

A further subject of the invention is a process for constructing a linearized vector characterized in that a vector with a polylinker is linearized with a restriction endonuclease, that oligo(dC) or oligo(dG) tails are added to the 3' ends, that a dideoxynucleotide residue is added to the ends of the oligo(dC) or oligo(dG) tails, that one of the oligo(dC) or oligo(dG) tails is cut off with a different restriction endonuclease and that an oligo(dT) tail is added to the free 3' end obtained.

The subject of the invention is in addition a process for constructing a cDNA library for which linearized vector molecules are hybridized via an oligo(dT) tail at one of their 3' ends to the poly(A) tail of mRNA molecules of a mRNA population, for which then doublestranded cDNA is synthesized from the mRNA molecules as template during enzymatic reactions and for which the vectors are recircularized in a way characterized by using linearized vector molecules which contain an oligo(dC) or oligo(dG) tail with a terminal dideoxynucleotide residue at their second 3' end.

Specialized examples for vectors containing a polylinker suitable for constructing linearized vectors according to the invention and for cloning cDNA according to the invented method are the plasmid pUC931 and the corresponding plasmids pOM1, pOM3, pOM9 as well as the plasmid pUC830 and the corresponding plasmids pOM2, pOM4 and pOM8.

Generally the term polylinker is used for short segments of DNA which contain at least two recognition sites for restriction endonucleases which are unique in the polylinker and do not occur in the vector.

In order to obtain a high yield with the method of the invention, polylinkers with at least two restriction sites for restriction endonucleases which do not produce recessed 3' ends can be used, because two steps have to be done during which deoxynucleotide tails are added.

The principle method for constructing plasmids pUC931 and pOM1 is given schematically in FIG. 1.

The vector pUC9 (deposited with the German Collection of Microorganisms (DSM), Göttingen, Federal Republic of Germany (FRG), depository number DSM No. 3421) is first cut with the restriction endonuclease HindIII which cuts only once in this plasmid. The protruding ends are filled-in with DNA polymerase I (Klenow fragment) in order to produce blunt ends.

This reaction causes a frame shift of +1 in the reading frame of the β-galactosidase gene which is located in this part of the vector. The vector thus treated is recircularized with T4 DNA ligase. The resulting plasmid is named pUC9(H−) and is cleaved with the restriction endonucleases PstI and EcoRI. In parallel, the vector M13tg131 (deposited with the German Collection of Microorganisms, depository number DSM 3494) is also cut with PstI and EcoRI. These reactions release the polylinker of M13tg131 which contains recognition sites for the restriction endonucleases PstI, SalI, BamHI, HindIII, XbaI, KpnI, SphI, EcoRV, SacI, SmaI. XmaI, EcoRI and for the corresponding isoschizomers. In the next step, the isolated polylinker from M13tg131 is inserted into the plasmid pUC9(H−) which has also been cut with PstI and EcoRI which corrects the frame shift. The sticky ends are covalently joined with T4 DNA ligase to produce plasmid pUC931.

The same principal construction scheme is used to obtain plasmid pOMI of the invention, but after the restriction digest with HindIII and the filling-in reaction with DNA polymerase I (Klenow fragment), a XhoI linker is inserted. The XhoI linker is synthesized according to per se known methods and represents the sequence 5' CTCGAG.

The essential difference between the vectors pUC931 and pOM1, pOM3, pOM9 of the invention is the existence of a stop codon in pUC931 in the region of the originally filled-in HindIII site while the vectors pOMI, pOM3 and pOM9 of the invention do not contain this stop codon (cf., FIG. 2). This implies that expression of the genetic information inserted into pUC931 is only possible in hosts with suppressor tRNAs (transfer RNA) which are mutated in such a way that their anticodon is complementary to the stop codon in pUC931.

The construction of the vectors pUC830 as well as pOM2, pOM4 and pOM8 of the done essentially according to the scheme in FIG. 1. In these cases the starting material are the plasmid pUC8 (deposited with the German Collection of Microoganisms, depository number DSM 3420) and the vector M13tg131 (deposited with the German Collection of Microorganisms, depository number DSM 3494). Compared with the vectors pUC931 and pOMI, the polylinker from M13tg131 is contained in the opposite orientation in the vectors pUC830, pOM2, pOM4 and pOM8. These vectors do not contain a stop codon (FIG. 2 and 3).

Figure 4:
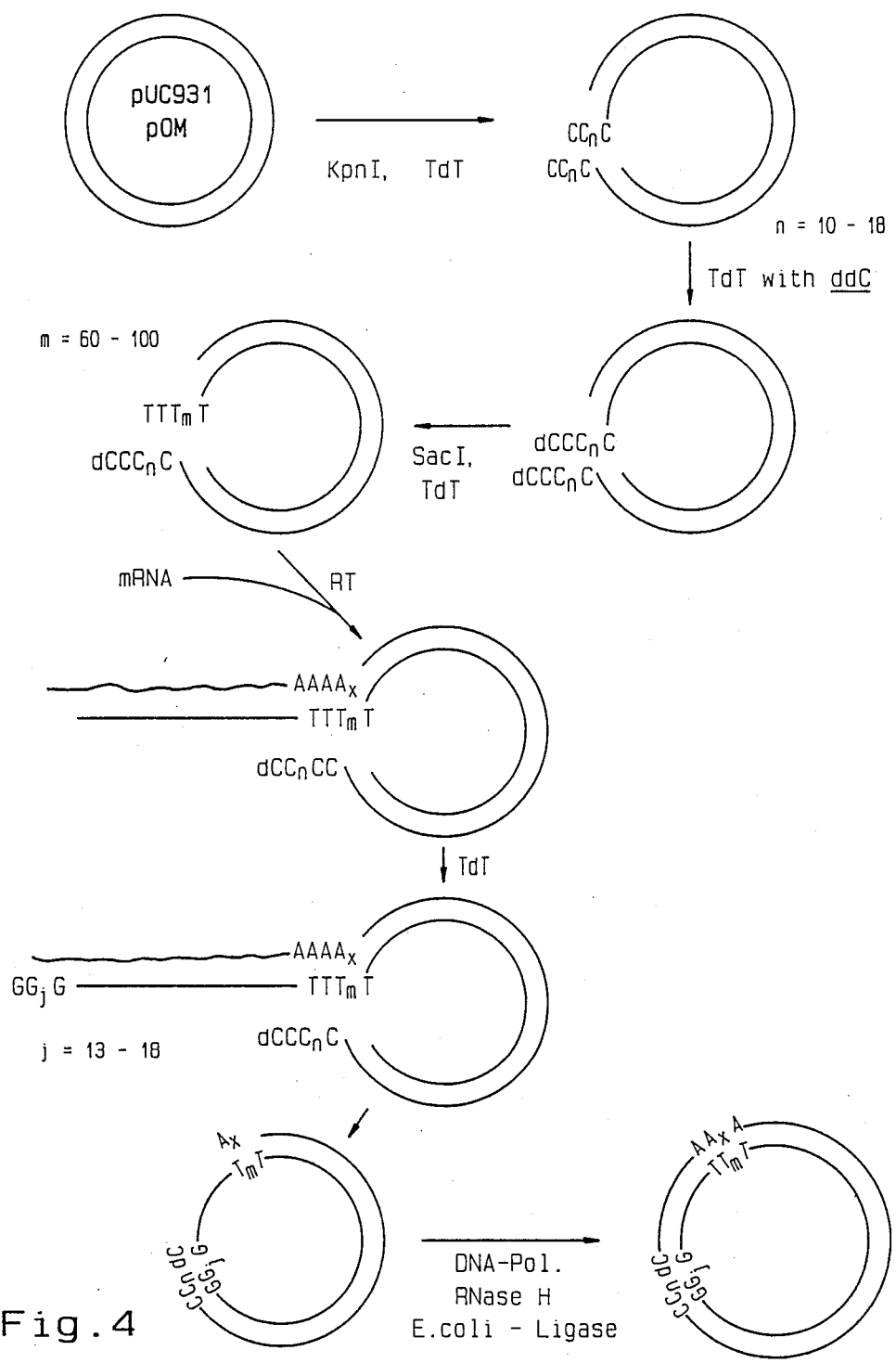
Figure 5:
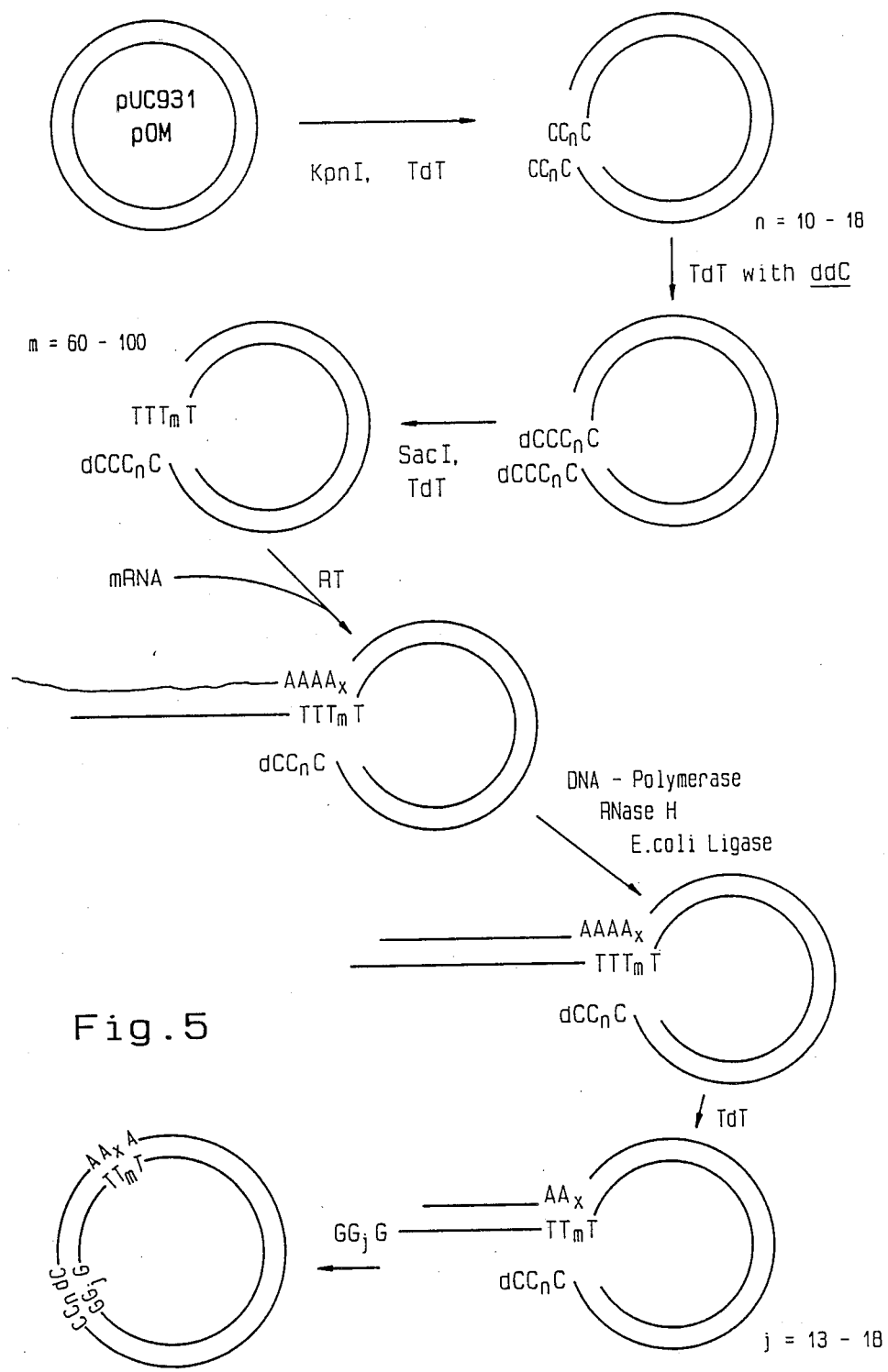

The vectors of the invention listed above serve as an example to explain the construction of cDNA libraries which consist of recombinant DNA molecules containing oriented, long cDNA inserts. According to the invention, high yields are obtained for the construction of cDNA libraries. The method of invention for constructing cDNA libraries is presented schematically in FIG. 4 and 5. If the plasmids pUC931 or pOMI of the invention are used, construction of a cDNA library starts with digesting these vectors with restriction endonuclease KpnI (FIG. 4 and 5, I and II). To the linearized plasmid obtained in this way. oligo(dC) tails are added with terminal transferase to the 3' ends of the doublestranded DNA in one embodiment of the invention (addition of dCTP). In another embodiment of the invention, the plasmid can also be tailed with dGTP.

In the next step a dideoxycytidine residue is added to the tails. This dideoxycytidine does not permit a further extension of the tails as it contains a hydrogen atom in its 3' position instead of an hydroxyl (OH−) group (FIG. 4 and 5, II).

According to the invention also other dideoxynucleotides can be used to block the tailed 3' ends.

In a preferred version, about 12 to 20 deoxycytidine residues are added for the tails (corresponding to n=10 to 18 in FIG. 4 and 5). The length of the tails can be checked by adding radioactive $^{32}$P-dCTP during the reaction with terminal transferase, cutting with a restriction endonuclease in the polylinker and analyzing the cut-off fragments on a polyacrylamide gel. The size of the tails can then be determined from suitable marker fragments run on the same gel.

In the next step according to the method of invention, the vector with oligo(dC) tails thus obtained is cut with a restriction endonuclease, thus producing an asymmetric molecule with only one oligo(dC) tail at one 3' end of the doublestranded DNA. To the free 3' end of this molecule an oligo(dT) tail is added with terminal transferase and dTTP. In a preferred embodiment of the method of invention this tail consists of 60 to 100 deoxythymidine residues (the number of nucleotides is given by m in FIG. 4 and 5). According to the process of invention the addition of dTTP can only occur at that 3' end which was produced by the second restriction endonuclease as the 3' end tailed with dCTP and ddCTP does not contain a 3' OH-group necessary for adding more nucleotides to the tail.

During the next step (FIG. 4 and 5 IV) a mRNA from a population of mRNAs from suitable cells is annealed via its poly(A) tail to the oligo(dT) tail of the linearized, asymmetric vector constructed as described above. The annealed mRNA is transcribed into the complementary first DNA strand with reverse transcriptase by addition of all four deoxynucleotides. In one embodiment (FIG. 4) of the invented process, the newly synthesized cDNA strand is then tailed with terminal transferase and dGTP. When compared with the state of the art, the process according to the invention has the advantage that recessed 3' ends of the first cDNA strand are more readily tailed with deoxyguanosine than with deoxycytidine residues (cf., FIG. 4 and 8). Then the oligo(dC) tail of the vector and the oligo(dG) tail of the cDNA strand are annealed. Finally, according to the method of invention, recombinant vector molecules with doublestranded cDNA inserts are produced by the enzymes DNA polymerase I, RNaseH and *E. coli* DNA ligase.

In a different embodiment of the method of invention, first the second strand is synthesized and then oligo(dG) tails are added to the first strand (FIG. 5). This procedure creates protruding 3' ends so that also an oligo(dC) tail can be added to this end with high efficiency. An oligo(dC) tail at the cDNA demands that a complementary oligo(dG) tail instead of an oligo(dC) tail is added to the linerized vector at the beginning to allow recircularization. The difference between the two embodiments of the method depicted in FIG. 4 and 5 and described above is only a different order of the last steps of the procedure.

According to the invention the methods described above yield different recombinant plasmids with cDNA inserts from a cellular mRNA population. These plasmids are transformed into appropriate host cells like *E. coli* K12 strains JM 83, DH1 or JM109. *E. coli* K12 strains JM 83 and DH1 are deposited with the American Type Tissue Collection (ATCC), Rockville Md., U.S.A. under accession numbers ATCC 35607 and ATCC 33849. *E. coli* K12 strain JM109 is deposited with the German Collection of Microorganisms (DSM), Mascheroder Weg 1b, D-3300 Braunschweig, German, under DSM number 3423. Plating of the transformed cells yields a cDNA library.

cDNA libraries according to the invention can be screened for expressed gene products. Depending on the *E. coli* strain used, isopropyl-β-D-thiogalactopyranoside (IPTG) has to be added to the agar for plating of the cDNA library. IPTG induces the expression of the γ-galactosidase operon in transformed hosts. Therefore expression of the enzyme in the host cells can yield fusion proteins from the cDNA inserts which consist of a N-terminal portion of β-galactosidase and a C-terminal portion coded for by the cDNA.

If the vectors pUC830 and pOM2, POM4, POM8 of the invention are used to construct cDNA libraries according to the invented method, essentially the procedure also follows the scheme presented in FIG. 4 and 5. The only difference results from the opposite orientation of the polylinker in these plasmids of invention. Therefore the first restriction digest has to be done with SacI instead of KpnI.

In summary the advantages of the invented process for constructing cDNA libraries with the invented vectors are as follows:

In the method given in FIG. 4, oligo(dG) tails are added with terminal transferase instead of oligo(dC) tails which are used in the prior art (cf., method of Okayama and Berg (loc. cit., FIG. 8)). The addition of oligo(dG) tails is more efficient for recessed 3' ends. With the embodiment of the method in FIG. 5 for constructing recombinant vectors with cDNA inserts, the oligo(dG) tails are added to protruding 3' ends which also works with dCTP with high efficiency. For the methods according to the invention, the tailing reaction for the addition of oligo(dG) tails is a step of the process which proceeds with higher efficiency than for the state of the art. Therefore also the yield of cDNA clones is higher for the method of invention than for the method of the prior art.

Figure 8:
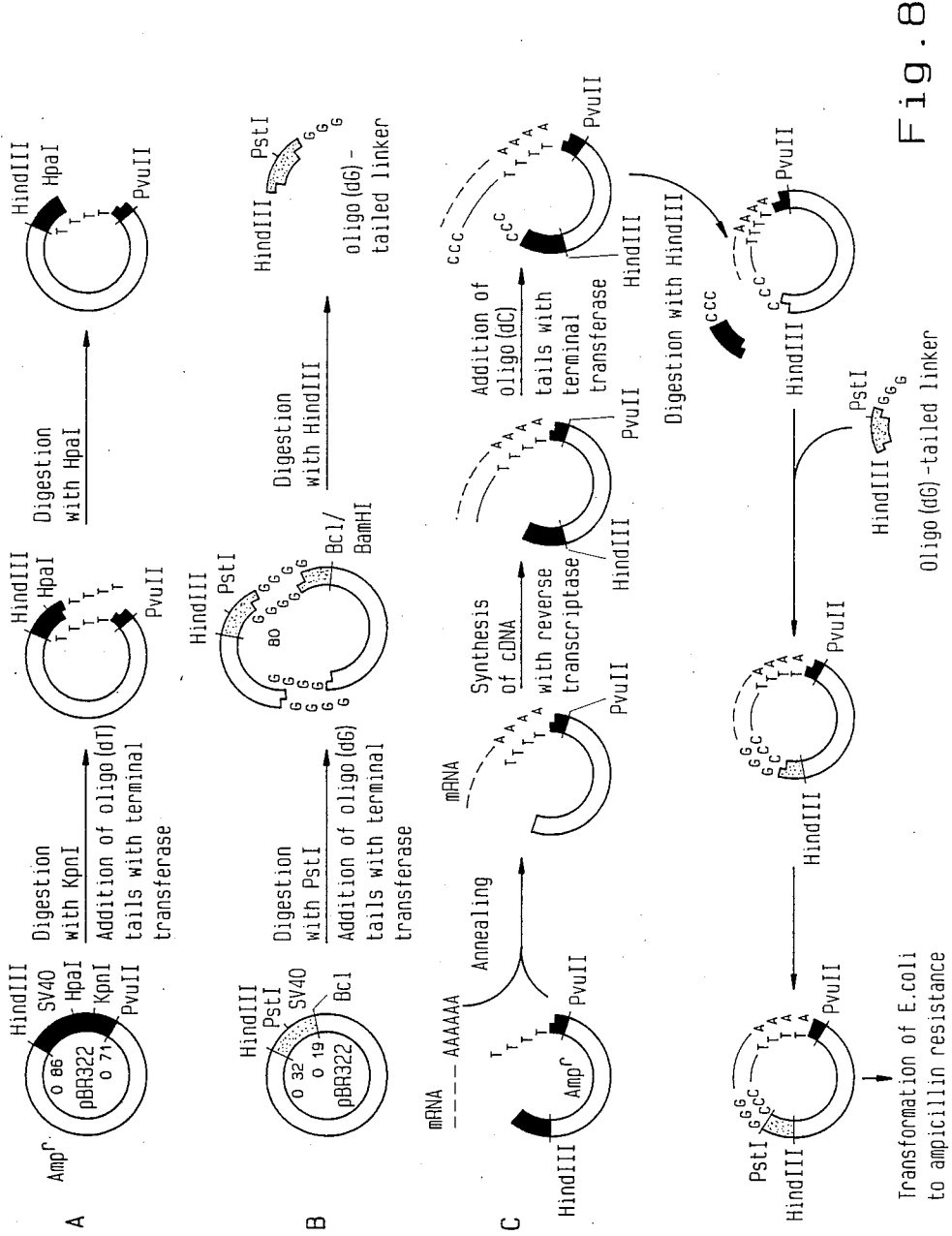

In contrast to the state of the art, in the method of invention all manipulations of the vector with restriction endonucleases are done before the mRNA is introduced into the process. For this reason the mRNA in the RNA/DNA hybrid cannot be cut by the restriction endonucleases, and therefore the method of invention will yield longer cDNA inserts which can also contain the complete genetic information for large proteins. An additional advantage of the method of invention is the fact that fewer steps are necessary, e.g., no special linker fragment with an oligo(dG) tail and a HindIII site has to be used as for the method of Okayama and Berg (FIG. 8).

The cDNA clones constructed according to the invention have in particular the advantage that the cDNA insert in the recombinant plasmid is located within the polylinker derived from the vector M13tg131. Therefore the insert is surrounded by several recognition sites for common restriction endonucleases which allow for easy recovery of the insert. For cDNA clones according to the state of the art recovery is difficult or impossible as only few or no restriction sites exist adjacent to the cDNA insert. The large number of unique restriction sites in the plasmids of the invention also facilitates restriction mapping of the cDNA inserts. Finally the cDNA clones constructed according to the invention can directly be sequenced from the 5' end of the insert by using commercially available "reverse sequencing primers" (E.Y. Chen and P.H. Seeburg, DNA 4 (1985), 165–170). This is not possible with cDNA clones constructed according to the method of Okayama and Berg (loc. cit.) as their vector does not contain sequences complementary to the commercial "reverse sequencing primers" flanking the 5' end of the inserted cDNA.

FIG. 1: Scheme of construction for the vectors pUC931 and pOMI

FIG. 2: Sequence of the polylinker from pUC931, pOMI, pOM3 and pOM9

FIG. 3: Sequence of the polylinker from pUC830, pOM2, pOM4 and pOM8

FIG. 4: Scheme of construction of a cDNA library

FIG. 5: Scheme of construction of a cDNA library

Figure 6:
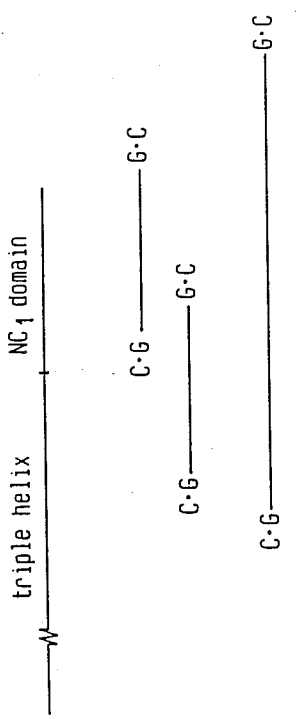

FIG. 6: Comparison of the lengths of cDNA clones constructed according to methods of the prior art and the method of invention FIG. 7: Scheme of construction of cDNA libraries where the cDNA is synthesized directly on free mRNA.

FIG. 8: Scheme of construction for cDNA libraries according to the method of Okayama and Berg The invention is illustrated by examples.

The enzymes used in the following examples were obtained from Boehringer Mannheim, Mannheim, FRG; Pharmacia, Freiburg, FRG or New England Biolabs, Bad Schwalbach, FRG. Reverse Transcriptase was bought from Life Science, Florida, U.S.A.

The enzymatic reactions were done according to manufacturer's instructions. The conditions are also described in T. Maniatis, E. F. Fritsch and J. Sambrook, "Molecular Cloning, A Laboratory Manual", Cold Spring Harbor (1982), New York.

EXAMPLE 1

Construction of the vector pUC931

2 μg of DNA of plasmid pUC9 (DMS 3421) are cut with 10 μof HindIII. Both protruding 5' ends are filled in with DNA polymerase I (Klenow fragment) and the resulting blunt ends are religated with 2μof T4 DNA ligase. This leads to a frame shift of +1.

*E. coli* K12 JM109 (DSM 3423) is transformed with the ligated plasmid, plated on plates with 5-Bromo-4- chloro-3-indolyl-β-D-galactoside (XGal) and IPTG and white colonies are isolated. Plasmid DNA from such colonies is isolated according to Birnboim and Doly (Nucl. Acids Res. 7 (1979), 1513–1522) to obtain plasmid pUC9(H−).

2 μg of plasmid pUC9(H−) are cut with 10 u each of PstI and EcoRI and centrifuged through a column of Sephacryl S-300 (Pharmacia) in a 1 ml syringe in order to separate the plasmid from its polylinker. Column chromatography is done according to the procedure of Maniatis et al. (loc. cit.) for Sephadex G 50 spun columns modified in such a way that centrifugation is done for 2 min at 1000 rpm in a Minifuge 2 (Christ, Osterode, FRG).

In a parallel reaction 2 μg of doublestranded DNA of M13tg131 (DSM 3494) are also cut with 10μ each of PstI and EcoRI. One tenth of the digested vector is labeled with 10μ of polynucleotide kinase, mixed with the nonradioactive material and run on a 5% polyacrylamide gel with tris/borate buffer (cf., Maniatis et al., loc. cit.). The polylinker of M13tg131 is isolated by electroelution in a dialysis bag after cutting the corresponding band out of the gel.

The polylinker obtained in this way is inserted with T4 DNA ligase into plasmid pUC9(H−) which has been cut with PstI and EcoRI as described.

Insertion of this polylinker from M13tg131 into pUC9(H−) induces a frame shift of −1 so that the initial reading frame of the region coding for β-galactosidase is restored. The original HindIII site which has been filled in as described gives rise to a stop codon (TAG) in the reading frame of the fragment coding for β-Galactosidase. Therefore expression of the genetic information inserted into pUC931 as a fusion protein with β-Galactosidase requires bacterial hosts which are supE and/or supF. E. coli JM109 carries the supE mutation.

Then cells of E. coli K12 JM109 (DSM 3423) are transformed with the ligation mixture described above and plated on yt-plates containing XGal, IPTG and 100 μg/ml ampicillin (cf., Maniatis et al., loc. cit.). The plasmid pUC931 is isolated from a weakly blue colony according to the method of Birnboim and Doly (loc. cit.).

The principle for constructing the vector pUC931 is schematically summarized in FIG. 1.

EXAMPLE 2a

Construction of the vector pOM1

According to known methods a XhoI linker with the DNA sequence CTCGAG is synthesized according to the phosphoramidite method. Plasmid pUC9 is cut with HindIII and the protruding ends are filled in with DNA polymerase I (Klenow fragment) as described in example 1. Unphosphorylated XhoI linker is ligated to the linear plasmid obtained before (R. Lathe et al., DNA 3 (1984), 173–182; A. Seth, Gene Anal. Techn. 1 (1984), 99–103). In this way only the 3' ends of the linker can be joined to the linearized plasmid which is done with T4 DNA ligase (cf., Maniatis et al.).

According to the invention all linkers with 3 or n×3 nucleotides are suitable for such an insertion because they cannot produce a frame shift. Such linkers should preferably contain restriction sites which do not occur in the polylinker from M13tg131 and which do not cut the vector. Further steps of the construction of plasmid pOMI are done as described in example 1 and FIG. 1. This implies that the vector pOMI differs from vector pUC931 only by the insertion of an additional XhoI recognition sequence in the filled-in HindIII site (cf., FIG. 1 and FIG. 2).

The inserted XhoI recognition sequence prevents the formation of a stop codon in the reading frame of the fragment coding for β-galactosidase. Therefore expression of genetic information inserted into this plasmid is also possible in bacterial hosts without suppressor tRNAs.

EXAMPLE 2b

Construction of vector pOM3 2 μg DNA of plasmid pUC9 (DSM 3421) are cut with HindIII as described in example 1. The 5' protruding ends are digested with 5μ of mung bean nuclease to produce blunt ends. As described in example 2a, an unphosphorylated ClaI linker (8 basepairs (bp)) is ligated to the vector thus prepared. The ClaI linker with the sequence CATCGATG is commercially available or can be synthesized according to per se known methods after the phosphoramidite method.

According to the invention, all linkers with 8 bp are suitable for such an insertion because deleting the 4 nucleotides on both ends of the cut HindIII site and inserting an 8 bp linker also results in a frame shift of +1 as in example 1. Preferable linkers for this insertion contain recognition sites for restriction endonucleases which do not cut in the polylinker of M13tg131 inserted afterwards and do not cut the vector.

Further reactions for constructing plasmid pOM3 are done as described in example 1 and FIG. 1. The plasmid pOM3 obtained in this way differs only by an additional ClaI site from vector pUC931. The insertion of the ClaI linker does not change the reading frame of the lacZα fragment of β-galactosidase. In addition another codon ATG is introduced in a different reading frame which could serve as internal start codon for expression of cDNA inserted in the polylinker.

After transformation of the construct with the inserted ClaI linker described above, a plasmid was isolated in which only the first of the four nucleotides of the HindIII site to the right of the ClaI linker had been removed. Thus 3 extra nucleotides in addition to the ClaI linker have been introduced which do not disturb the reading frame. They are overlined in FIG. 2.

EXAMPLE 2c

Construction of the vector pOM9

Plasmid pUC9 is cut with HindIII as described before. Then only one nucleotide (dA) is filled in with DNA polymerase I (Klenow fragment). The residual three protruding nucleotides are removed at both ends with mung bean nuclease and the resulting blunt ends are religated. This construction also gives a frameshift of +1. In addition a new palindromic sequence CAATTG is created for which, unfortunately, no restriction enzyme is known yet. This sequence does not occur in pUC9 or in the polylinker of M13tg131 and would therefore also provide a unique restriction site.

Further steps for constructing plasmid pOM9 are done as described in example 1 and FIG. 1. The reading frame of the lacZα fragment of β-galactosidase is conserved.

EXAMPLE 3

Construction of the vectors pUC830 and pOM2, pOM4, pOM8

Starting with 2 μg DNA of plasmid pUC8 (DSM 3420), vector pUC830 is constructed as explained in example 1. The vector pUC830 differs therefore from pUC931 in containing the polylinker of M13tg131 in the opposite orientation.

With 2 μg of DNA of pUC8 each of the vectors pOM2, pOM4 and pOM8 are constructed as described in examples 2a, 2b and 2c. All these vectors (cf., FIG. 3) do not contain a stop codon and do not disturb the reading frame of the lacZα fragment of β-galactosidase.

The plasmid pOM4 also contains three additional nucleotides on the left side of the inserted ClaI linker because, as in pOM3, only one nucleotide of the protruding end produced with HindIII was removed. In addition the last nucleotide, dG, of the ClaI linker was mutated to dT so that no additional start codon ATG behind the polylinker is introduced which could have anyhow disturbed expression of the inserted cDNA. The three additional nucleotides and the mutated nucleotide are overlined in FIG. 3.

EXAMPLE 4

Construction of linearized vector

400 μg of DNA of vector pUC931 are cut with 200μ KpnI and tailed with dCTP and 200μ terminal transferase (FIGS. 4 and 5).

To determine the length of the oligo(dC) tails, an aliquot of the plasmid is cut with BamHI and run on a 10% polyacrylamide gel together with oligonucleotides of known lengths.

In this way the reaction conditions are optimized so that the number of deoxycytidine residues in the tails is in the range of 10 to 20. Vector molecules with oligo(dC) tails of the desired length are then tailed with terminal transferase and dideoxynucleoside triphosphates derivatives. If ddCTP is used, the linearized plasmid contains a terminal ddC at both oligo(dC) tails. Therefore these tails cannot be extended in further reactions with terminal transferase.

The oligo(dC) tail at the 3' end of the noncoding strand is cut off with 100μ SacI, resulting in an asymmetric product (cf., FIG. 4 and 5) which can be purified by chromatography on oligo-dI cellulose (Pharmacia).

The asymmetric linearized vector is tailed with terminal transferase and dTTP. This adds an oligo(dT) tail to the 3' end of the noncoding strand. The reaction conditions are chosen in such a way that this tail contains about 60 to 100 thyonidine residues. The tailed vector can be purified by chromatography on oligo-dA cellulose (Pharmacia).

EXAMPLE 5

Construction of a cDNA librarY with the tailed vector mRNA is isolated according to per se known methods and mixed with the linearized asymmetric vector prepared according to example 4, for instance 1 to 2 μg poly(A) RNA from PYS-2 cells (mouse) per μg of vector DNA. The mixture is heated for 10 min to 57° C. in 150 mM KCl, 50 mM tris/HCl, pH 8.3. During cooling down a mixture of linearized vector molecules is produced, each with a mRNA molecule hybridized to the oligo(dT) tails.

For the following synthesis of the first DNA strand (complementary to the mRNA), reverse transcriptase and dATP, dTTP, dGTP and dCTP are used.

The newly synthesized cDNA strand is then tailed with terminal transferase and dGTP to add 15 to 20 nucleotides. Standard conditions (cf., Maniatis et al., loc. cit.) are used to anneal the oligo(dC) tail of the vector with the oligo(dG) tail of the cDNA. This results in doublestranded, circular recombinant vector molecules with a RNA/DNA hybrid insert (cf., FIG. 4).

During the next reaction the mRNA strand in the molecule is replaced by the second cDNA strand. This is done with the enzymes DNA polymerase I, RNaseH and E. coli ligase together with dATP. dTTP, dCTP and dGTP (U. Gubler and B. J. Hoffman, Gene 25 (1983), 283–286).

These reactions described above result in a family of recombinant, doublestranded vectors with a doublestranded cDNA insert. The DNA strands are not covalently linked at the position of ddC nucleotide in the vector. This gap is closed later on in the daughter molecules during replication in the bacterial host.

This mixture of recombinant vectors with cDNA inserts is preferentially transformed, according to known methods, into a recA⁻ host like E. coli K12 DH1 (ATCC 33849) or E. coli K12 JM109 (DSM 3423) (Maniatis et al., loc. cit.). The transformants are plated according to known methods onto nitrocellulose filters (Schleicher & Schuell, Dassel, FRG) placed on yt-plates with 100 μg/ml ampicillin. The plates are incubated over night at 37° C.

The colonies obtained represent clones of cells each transformed with a recombinant vector molecule with a cDNA insert. The term cDNA library refers to all these colonies.

The colonies of such a cDNA library can be washed off from the filters and be frozen for storage as amplified bacterial suspension with 15% glycerol. Aliquots of this suspension can be thawed and plated again when needed.

For sequencing positive clones from the cDNA library constructed as described above, the corresponding colonies are grown up and plasmid DNA is isolated from the cultures after Birnboim and Doly (loc. cit.). The DNA sequence of the cDNA inserts in these plasmids can be determined according to Maxam and Gilbert after the method of Ruther et al. (Nucl. Acids Res. 9 (1981), 4087–4097) or according to Sanger et al. (J. Mol. Biol. 143 (1980), 161–178) with commercially available primers.

The cDNA inserts can also be subcloned into other vectors for sequencing.

EXAMPLE 6

Construction of additional cDNA libraries with vector pUC931

Two cDNA libraries, cI and cII, are constructed according to examples 4 and 5 with the vector pUC931 and mRNA from the murine cell line PYS-2.

150 μg of poly(A) RNA are loaded on a sucrose gradient (10% to 36% sucrose) and centrifuged in a Beckman ultracentrifuge L8-70 in a SW 28 rotor for 21 hours at 26 000 rpm. Fractions of 1.2 ml are collected, the poly(A) RNA precipitated for each fraction and redissolved in RNase- free, sterile H₂O. One tenth of the fractions 20 to 25 is pooled and used to construct the cDNA library cI, while one tenth of the fractions 26 to 32 is pooled for constructing the cDNA library cII. For each library 0.3 μg of vector pUC931 are used. *E. coli* K12 DH1 serves as host for the recombinant plasmids with cDNA inserts.

The plated cDNA library is screened with a synthetic oligonucleotide as described in Oberbaumer et al. (Eur. J. Biochem. 147 (1985), 217–224).

From the cDNA library cI a clone pAI4 is isolated with a cDNA insert of 1.6 kb. Clone PAI5 is obtained from library cII and contains a cDNA insert of 2.6 kb (cf., FIG. 6).

The 5' ends of the clones are characterized by sequencing according to Sanger et al. as described in example 5. The sequence confirms that clones pAI4 and pAI5 code for the α1 chain of collagen type IV. Clone pAI5 contains the complete 3' untranslated region and the sequences coding for the NC1 domain and for the C-terminal triple helix.

All clones for the α1 chain of collagen IV published thus far do not contain more than about 200 bp coding for the triple helix and many of them cover only untranslated sequences. In the past cDNA clones of similar size as e.g., clone pA15 have only been obtained with size fractionated cDNA and highly enriched mRNA (H. Lehrach et ,al., Proc. Natl. Acad. Sci. USA 75 (1978) 5417–5421; T. Pihlajaniemi et al., J Biol. Chem. 260 (1985) 7681–7687). The longest cDNA clone for the α1 chain of collagen type IV which was obtained from a cDNA library constructed after Okayama and Berg (loc. cit.) contained only an insert of 1.3 kb (Y. Yamada, personal communication; cf., FIG. 6).

I claim:

1. A process for constructing a cDNA library comprising
    a. linearizing a vector containing a polylinker by treatment with restriction endonuclease,
    b. adding oligo(dC) or oligo(dG) tails to the 3' ends,
    c. adding dideoxynucleotide residues to the oligo(dC) or oligo(dG) tails,
    d. removing one of the oligo(dC) or oligo(dG) tails at the 3' end with a different restriction endonuclease,
    e. adding an oligo(dT) tail to the free 3' end,
    f. hybridizing linearized vector molecules via the oligo (dT) tail of step (e) to the poly(A) tail of mRNA molecules of a mRNA population,
    g. synthesizing double stranded cDNA from the mRNA molecules as template,
    h. adding an oligo(dC) or oligo(dG) tail to one of said cDNA strands,
    i. recircularizing said vector by annealing said oligo (dC) or oligo(dG) tail with a dideoxynucleotide-tailed complementary oligo(dG) or oligo(dC) tail on the other 3' end, and
    j. transforming a microorganism with the vector of step (i).

2. A population of microorganisms containing a cDNA library constructed according to claim 1.

3. A linearized vector comprising an oligo(dT) tail at one 3' end and an oligo(dC) or oligo(dG) tail with a terminal dideoxynucleotide at the other 3' end.

4. A linearized vector according to claim 3 comprising an oligo(dC) or oligo(dG) tail consisting of 20 cytidine or guanosine residues.

5. A linearized vector according to claim 3 comprising an oligo(dT) tail consisting of 60 to 100 thymidine residues.

6. A process for constructing a vector according to claim 3 comprising:
    a. linearizing a vector containing a polylinker by treatment with restriction endonuclease,
    b. adding oligo(dC) or oligo(dG) tails to the 3' ends,
    c. adding dideoxynucleotide residues to the oligo(dC) or oligo(dG) tails,
    d. removing one of the oligo(dC) or oligo(dG) tails at the 3' end with a different restriction endonuclease, and
    e. adding an oligo(dT) tail to the free 3' end.

7. A process according to claim 6 wherein said vector containing a polylinker is selected from the group consisting of plasmids pUC931, pUC830, pOM1, pOM2, pOM3, pOM4, pOM8, and pOM9.

8. The vector pUC931.

9. A vector selected from the group consisting of: pOM1, pOM3 and pOM9.

10. The vector pUC830.

11. A vector selected from the group consisting of: pOM2, pOM4 and pOM8.

* * * * *